(12) United States Patent
Rhim et al.

(10) Patent No.: US 8,470,558 B1
(45) Date of Patent: Jun. 25, 2013

(54) **USE OF MAMMALIAN EXPRESSION VECTOR INCLUDING T7 PROMOTER AND N-TERMINAL HA TAG FOR OVEREXPRESSION OF HUMAN GENES IN *E. COLI***

(71) Applicant: Catholic University Industry-Academic Cooperation Foundation, Seoul (KR)

(72) Inventors: Hyang-Shuk Rhim, Seoul (KR); Goo-Young Kim, Seoul (KR); Jeong-Mi Moon, Suncheon-si (KR)

(73) Assignee: Catholic University Industry-Academic Cooperation Foundation, Seoul (KR)

( * ) Notice: Subject to any disclaimer, the term of this patent is extended or adjusted under 35 U.S.C. 154(b) by 0 days.

(21) Appl. No.: 13/664,465

(22) Filed: Oct. 31, 2012

(30) Foreign Application Priority Data

Jul. 27, 2012 (KR) .................. 10-2012-0082718
Jul. 27, 2012 (KR) .................. 10-2012-0082719

(51) Int. Cl.
*C12P 21/06* (2006.01)

(52) U.S. Cl.
USPC ...................................... 435/69.1

(58) Field of Classification Search
USPC ........................................................ 435/69.1
See application file for complete search history.

(56) References Cited

PUBLICATIONS

Jeong-Mi Moon et al., A new idea for simple and rapid monitoring of gene expression: requirement of nucleotide sequences encoding an Nterminal HA tag in the T7 promoter-driven expression in *E. coli*, Biotechnol Lett DOI 10.1007/s10529-012-0966-8, Springer, Jun. 20, 2012.

*Primary Examiner* — Maryam Monshipouri
(74) *Attorney, Agent, or Firm* — Lexyoume IP Meister, PLLC.

(57) ABSTRACT

The present invention relates to a technique for the T7 promoter-driven expression of a foreign protein, preferably, a human protein in *E. coli* having no T7 RNA polymerase. More particularly, the present invention relates to use of a vector including a T7 promoter and an N-terminal HA tag sequence for overexpression of a foreign protein in *E. coli* having no T7 RNA polymerase, *E. coli* that includes the vector and is able to overexpress the foreign protein in the absence of T7 RNA polymerase, a method for expressing or producing the foreign protein using the *E. coli*, and a method for analyzing functions of the foreign protein. Further, the present invention relates to a simple, rapid method for evaluating the expression and cytotoxicity of a human protein in *E. coli* by using the vector.

7 Claims, 6 Drawing Sheets

[FIG. 1d]

USE OF MAMMALIAN EXPRESSION VECTOR INCLUDING T7 PROMOTER AND N-TERMINAL HA TAG FOR OVEREXPRESSION OF HUMAN GENES IN *E. COLI*

CROSS REFERENCE TO RELATED APPLICATION

This application claims priority to and the benefit of Korean Patent Application No. 10-2012-0082718 filed on Jul. 27, 2012 and Korean Patent Application No. 10-2012-0082719 filed on Jul. 27, 2012, which are hereby incorporated by reference for all purposes as if fully set forth herein.

BACKGROUND OF THE INVENTION (a) Field of the Invention

The present invention relates to a technique for the T7 promoter-driven expression of a foreign protein, preferably, a human protein in *E. coli* having no T7 RNA polymerase. More particularly, the present invention relates to use of a vector including a T7 promoter and an N-terminal HA tag sequence for overexpression of a foreign protein in *E. coli* having no T7 RNA polymerase, *E. coli* that includes the vector and is able to overexpress the foreign protein in the absence of T7 RNA polymerase, a method for expressing or producing the foreign protein using the *E. coli*, and a method for analyzing functions of the foreign protein. Further, the present invention relates to a simple, rapid method for evaluating the expression and cytotoxicity of a human protein in *E. coli* by using the vector.

(b) Description of the Related Art

From physiological, biochemical and genetic perspectives, *E. coli* (*Escherichia coli*) is one of the most well characterized bacteria, and is a useful strain for the production of recombinant proteins or their functional studies in biotechnology. The use of *E. coli* in the production of recombinant proteins has many advantages of high production efficiency and a reduction in time and cost. However, when a vector having a heterogeneous promoter is introduced into *E. coli*, and components required for expressing the protein do not exist in the endogenous *E. coli* gene expression system, the target protein is not produced in *E. coli*.

Representative examples thereof include the pcDNA and pCS2+ mammalian expression vectors widely used for molecular cloning. These vectors contain the cytomegalovirus (CMV) promoter and the bacteriophage T7 and/or SP6 promoter(s) to drive transcription of genes in mammalian cells and in vitro, respectively. The bacteriophage T7 promoter is known to be much stronger than the *E. coli* promoter, but it has an extremely high specificity for intrinsic T7 RNA polymerase (T7 RNAP). Thus, when an expression vector utilizing the T7 promoter is transformed into *E. coli* having lacking T7 RNAP, target protein is hardly expressed. In particular, T7 promoter-driven gene transcription is known to rarely occur in *E. coli* DH5α and TOP10 strains lacking T7 RNAP, which are widely used in molecular cloning (Melton, D. A., et al., 1984. 12(18): p. 7035-56; Studier, F. W. and B. A. Moffatt, J Mol Biol, 1986. 189(1): p. 113-30; Chamberlin, M., J. McGrath, and L. Waskell, Nature, 1970. 228(5268): p. 227-31; McAllister, W. T., Cell Mol Biol Res, 1993. 39(4): p. 385-91).

Therefore, these vectors have not been used for the expression of the cloned gene in *E. coli*, but mainly used for increasing the copy number of the plasmid DNA through replication of the vector plasmid DNA in *E. coli*. Alternatively, for the T7 promoter-driven expression of the cloned gene from the vector, *E. coli* should be transformed by introduction of a T7 RNAP gene or by insertion of the T7 RNAP gene under the control of the *E. coli* lac promoter in order to utilize the T7 promoter in *E. coli*.

The related art patents, Korean Patent No. 0262867 discloses that T7 promoter-driven expression of recombinant human granulocyte-colony stimulating factor in *E. coli* is achieved by using *E. coli* BL21 (DE3) transformed to express T7 RNAP as a host cell and a vector having the lac operator placed downstream of the T7 promoter, and Korean Patent No. 0389378 discloses that T7 promoter-driven expression of CSBP-2 (Cytokine-Suppressive Anti-inflammatory Drug-Binding Protein 2) in *E. coli* is achieved by using *E. coli* BL21 (DE3) transformed to express T7 RNAP as a host cell and culturing the *E. coli* at low temperature. As such, the conventional methods have the problem of requiring *E. coli* with T7 RNAP for T7 promoter-driven expression of foreign proteins in *E. coli*.

If recombinant proteins can be expressed from the mammalian expression vector pcDNA using the endogenous *E. coli* gene expression system in the absence of T7 RNAP, it is possible to express human genes in a wide range of *E. coli* strains as well as in mammalian cells, and it is also expected to bring tremendous progress in functional studies of proteins or mass production of industrially useful proteins by means of *E. coli*.

SUMMARY OF THE INVENTION

An object of the present invention is to provide a technique for overexpressing a foreign protein in *E. coli* having no T7 RNA polymerase by using a mammalian expression vector including a T7 promoter and an N-terminal HA tag sequence. According to the present invention, it is possible to provide a method for expressing and producing a foreign protein in *E. coli* using the vector, which overcomes the phenomenon of the known cell type-specific promoter inducing expression.

More particularly, an object of the present invention is to provide a composition for overexpressing a foreign protein in *E. coli* having no T7 RNA polymerase, comprising the vector that sequentially includes the T7 promoter, a base sequence encoding the HA tag, and a gene encoding the foreign protein in the 5' to 3' direction.

Another object of the present invention is to provide *E. coli* expressing the foreign protein from the vector, which contains the T7 promoter, the N-terminal HA tag, and the gene encoding the foreign protein and does not contain a T7 RNA polymerase.

Still another object of the present invention is to provide a method for expressing and producing the foreign protein driven by the vector in *E. coli*.

Still another object of the present invention is to provide a method for analyzing the functions of the foreign protein by culturing the *E. coli*.

Still another object of the present invention is to provide a composition and a method for assessing cytotoxicity of the target gene or screening anti-cytotoxic substances using the vector system.

BRIEF DESCRIPTION OF THE DRAWINGS

FIG. 1d is the result showing the comparison of E. coli growth, in which 1 ng of each plasmid was transformed into E. coli DH5α, and then the number of colonies formed was counted;

DETAILED DESCRIPTION OF THE PREFERRED EMBODIMENTS

Figure 1A:
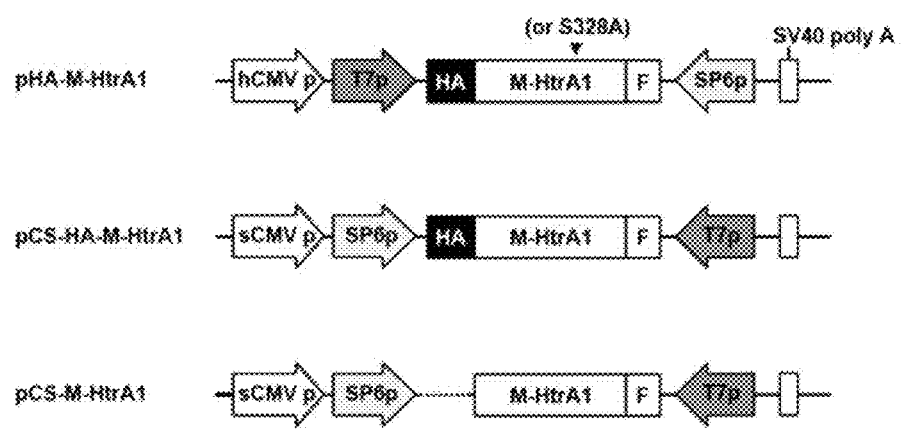
FIG. 1a is a schematic representation of various mammalian expression vectors including mature high temperature requirement A1 (M-HtrA1) gene that was constructed in the present invention, in which S328A indicates a mutant generated by replacing the 328-serine residue of HtrA1 with alanine, h indicates human, s indicates simian, p indicates promoter, and GST indicates glutathione S-transferase.

The present invention relates to a technique for the T7 promoter-driven expression of a foreign protein, preferably a human protein, in E. coli having no T7 RNA polymerase.

HtrA1 (High temperature requirement A1) is a serine protease highly conserved from bacteria to humans. HtrA1 exists as a zymogen, and matures to an active form having a protease activity through processing of its N-terminal region. It is known that HtrA1 overexpression in mammalian cells induces cell death in a serine protease-dependent manner.

For functional studies of HtrA1 in the cytoplasm, the present inventors cultured E. coli harboring the HtrA1-encoding gene cloned into a pcDNA3 plasmid. Surprisingly, they found that the growth of E. coli is suppressed in a serine protease-dependent manner due to the expression of HtrA1 driven by the vector in E. coli.

In order to investigate what elements of the plasmid function as cis-acting elements for HtrA1 expression in E. coli in the absence of T7 RNAP, the present inventors performed experiments using a variety of combinations of promoters, targets gene and tags. They demonstrated for the first time that expression of the target genes from the mammalian vector system in E. coli is directed by the combination of both the T7 promoter and nucleotide sequences encoding the N-terminal HA tag (FIG. 1). Furthermore, the present inventors demonstrated that this phenomenon is not specific to HtrA1, and different target genes are also successfully expressed even though HtrA1 is replaced with different target genes in the vector system including the T7 promoter and the N-terminal HA tag (FIG. 2).

These results indicate that the T7 promoter and nucleotide sequences encoding the N-terminal HA tag are cis-acting elements responsible for the expression of foreign genes placed downstream. In particular, the present inventors demonstrated for the first time that the conventional HA tag sequence used for purification and detection of recombinant proteins surprisingly functions to induce and promote the expression of foreign genes. Therefore, they developed a novel vector system for the T7 promoter-driven expression of foreign proteins by introducing the vector including T7 promoter, N-terminal HA tag, and a foreign protein-encoding gene into E. coli having no T7 RNAP, thereby completing the present invention.

The vector system of the present invention allows the T7 promoter-driven expression and production of recombinant proteins by using the endogenous E. coli gene expression system even though T7 RNAP does not exist in E. coli, and thus it can be used for functional studies of proteins or mass production of industrially useful proteins by means of E. coli.

Furthermore, the vector system of the present invention can be used for the purpose of pre-testing the expression of target genes in E. coli before applying it to mammalian cells. Generally, it takes at least 1 week to investigate expression directed from the mammalian expression vector and functions of the target genes in mammalian cells after molecular cloning, but a pre-test in E. coli is performed using the vector system of the present invention, thereby minimizing the experiment time (preferably, measured within 24 hours) and evaluating the expression and functions of target genes more efficiently.

Practically, the present inventors examined the expression of HtrA1 from the vector system of the present invention in both E. coli and mammalian cells. As a result, it was found that HtrA1 known to induce cell death of mammalian cells also induces the growth suppression of E. coli (FIGS. 1, 3 and 4). These results indicate that the expression and functions of target gene are consistent in both mammalian cells and E. coli strain, and suggest that the vector system of the present invention can be applied as a pre-test system in E. coli.

Moreover, the vector system of the present invention can be used for the screening target genes having the specific functions. In one preferred embodiment, the vector of the present invention can be used as a screening system for rapid evaluation of cytotoxicity of genes by applying it in a pre-test step for screening genes showing cytotoxicity or inducing cell death in mammalian cells.

Hereinafter, the present invention will be described in more detail.

In one aspect, the present invention relates to a composition for overexpressing a foreign protein in E. coli, comprising the vector that sequentially includes the T7 promoter, the HA tag, and a gene encoding the foreign protein in the 5' to 3' direction.

In another aspect, the present invention relates to E. coli expressing the foreign protein from the vector, in which the E. coli contains the above described vector including sequentially the T7 promoter, the HA tag, and the gene encoding the foreign protein in the 5' to 3' direction, and does not contain a T7 RNA polymerase.

Preferably, the *E. coli* used as a host cell to be transformed with the vector of the present invention may be an *E. coli* that does not express a foreign gene or expresses it at a very low level using its endogenous gene expression system under the control of T7 promoter because of the absence of T7 RNA polymerase. Example of the *E. coli* may include *E. coli* DH5α strain, *E. coli* TOP10 strain, *E. coli* JM109 strain, *E. coli* XL1-Blue strain or the like, but is not limited thereto.

As used herein, the term "vector" refers to a recombinant vector capable of expressing a foreign protein in a suitable host cell, preferably, in *E. coli*, and to a gene construct that includes essential regulatory elements to which a foreign gene is operably linked in such a manner as to be expressed. The vector may be plasmids, phage particles, or simply potential genomic inserts. As used herein, "plasmid" and "vector" are sometimes used interchangeably as the plasmid is the most commonly used form of vector at present. With respect to the objects of the present invention, a plasmid vector is preferably used.

As used herein, the term "operably linked" refers to a functional linkage between a nucleic acid expression control sequence and a foreign protein-encoding nucleotide sequence in such a manner as to allow general function to occur. For example, the T7 promoter and HA tag are regions of inducing and regulating the expression of the foreign protein-encoding nucleotide sequence placed downstream thereof, and are operably linked to the foreign protein-encoding nucleotide sequence. A recombinant vector may be generated using a genetic recombinant technique well known in the art.

The vector of the present invention is characterized by including the T7 promoter and N-terminal HA tag as a region for inducing the expression of foreign proteins. In particular, the conventional HA tag has been used as a means for easy purification and detection of expressed proteins. However, it was first demonstrated that the HA tag sequence is able to induce and promote the expression of foreign proteins when it is placed downstream of T7 promoter and at the 5' region of the foreign protein-encoding sequence in the present invention.

As used herein, the term "promoter" refers to an untranslated DNA sequence usually located upstream of the coding region, which contains the binding site for polymerase and initiates transcription of the gene downstream of the promoter into mRNA. The promoter used in the present invention is characterized by T7 promoter.

The T7 promoter refers to a promoter derived from a bacteriophage T7. Preferably, the T7 promoter may have a base sequence of SEQ ID NO. 1.

Further, the HA tag of the present invention refers to a fragment derived from human influenza hemagglutinin. Conventionally, the HA tag is included in an expression vector to be used as a tag for easy purification and detection. In the present invention, however, the HA tag is placed at the 5'-adjacent region of the foreign protein-encoding region, and used for inducing and promoting the expression of foreign genes. The HA tag may have an amino acid sequence of SEQ ID NO. 2 (YPYDVPDYA), and may be preferably encoded by a base sequence of SEQ ID NO. 3 (TAC CCT TAC GAT GTA CCG GAT TAC GCA).

Further, the promoter and HA tag sequences of the present invention may include sequence variants that show substantially equivalent activity in the induction of foreign protein expression, even though there are some differences in the sequences. For example, the sequence variant may be a sequence variant having a homology of 70% or more, preferably 80% or more, more preferably 90% or more, and much more preferably 95% or more with the sequence of SEQ ID NO. 1, 2, or 3.

For expression, the nucleotide sequence encoding the foreign protein is inserted downstream of the promoter and HA tag in the vector of the present invention. The foreign protein to be expressed by the vector of the present invention is not particularly limited, and any of the proteins desired by those skilled in the art can be applied. Specific Examples thereof may include peptides, polypeptides, binding proteins, binding domains, adhesion proteins, structural proteins, regulatory proteins, toxin proteins, enzymes, enzyme inhibitors, hormone, hormone analogues, antibodies, signal transduction proteins, single chain antibodies, antigens, cytokines, regulators or parts thereof or the like.

In a specific embodiment of the present invention, HtrA1 (high temperature requirement protein A1; Genbank Accession No. NM_002775), XIAP (X-linked inhibitor of apoptosis protein; Genbank Accession No. BC032729), MIF (macrophage migration inhibitory factor; Genbank Accession No. AF469046) and Parkin (Genbank Accession No. AB009973) proteins were successfully expressed using the vector system of the present invention in *E. coli*, respectively. However, these are illustrative only, and the scope of the present invention is not limited thereto.

The vector of the present invention may further include a replication origin for effective replication into several hundreds of plasmid vectors per host cell, a selectable marker for selecting host cells introduced with the vector (e.g., antibiotic resistance genes, auxotrophic marker genes, etc), a polyadenylation signal, a signal sequence, an enhancer, a signal sequence for membrane targeting or secretion, and restriction enzyme sites into which a fragment of foreign DNA may be inserted. If proper restriction enzyme sites do not exist, the vector and foreign DNA can be easily ligated using synthetic oligonucleotide adaptors or linkers in accordance with the conventional methods.

The method for generating the vector system of the present invention is not particularly limited, but in one embodiment, the vector system of the present invention can be more easily generated by using a commercially available T7 promoter-containing vector as a basic vector. For example, a pcDNA or pRSET series vector may be used. These vectors include T7 promoter, and thus the vector system of the present invention can be constructed by inserting the HA tag sequence at the adjacent region and a sequence encoding the desired protein downstream thereof.

The vector system of the present invention thus constructed may be used for expressing or producing foreign proteins in both *E. coli* and mammalian cells, and used for functional studies of foreign proteins unidentified with regard to cell proliferation and death. The vector system of the present invention can be also used for pre-testing the expression of target genes in *E. coli* before applying it to mammalian cells, and furthermore, can be used for assessing target genes having specific functions.

In one aspect using the vector system of the present invention, the present invention relates to a method for expressing or producing foreign protein, including the step of culturing *E. coli* harboring the vector.

Preferably, the present invention relates to a method for producing a foreign protein, comprising the step of culturing *E. coli* that contains a vector sequentially including a T7 promoter, a nucleotide encoding an HA tag and a gene encoding a foreign protein in the 5' to 3' direction, and does not contain a T7 RNA polymerase.

As used herein, the term "introduction" of the vector into *E. coli* means that a foreign DNA is delivered inside *E. coli*, and encompasses transformation, transfection, and transduction. The method of introducing the vector of the present invention into *E. coli* includes any introduction method of nucleic acid into cells, and may be performed using a suitable standard technique known in the art. Examples thereof may include electroporation, calcium phosphate precipitation, calcium chloride precipitation, retroviral infection, microinjection, a cationic liposome-mediated method, dextran sulfate-, lipofectamine-, and desiccation/inhibition-mediated transformation or the like, but are not limited thereto.

The *E. coli* harboring the vector system of the present invention may be cultured by the method typically used in the art, and the culture method includes batch culture, continuous culture, and fed-batch culture, but is not limited thereto. The media used in the culture may be readily adjusted according to the strain selected by those skilled in the art, and commercial media may be used. The media include a variety of carbon sources, nitrogen sources, and trace elements. Examples of the carbon sources include carbohydrates such as glucose, sucrose, lactose, fructose, maltose, starch, and cellulose, oils such as soybean oil, sunflower oil, castor oil and coconut oil, fatty acids such as palmitic acid, stearic acid, and linoleic acid, alcohols such as glycerol and ethanol, and organic acid such as acetic acid. These carbon sources may be used alone or in combinations thereof. Examples of the nitrogen sources include an organic nitrogen source such as peptone, yeast extract, meat extract, malt extract, corn steep liquor, soy meal, and an inorganic nitrogen source such as urea, ammonium sulfate, ammonium chloride, ammonium phosphate, ammonium carbonate and ammonium nitrate. These nitrogen sources may be used alone or in combinations thereof. The media may include potassium dihydrogen phosphate, dipotassium hydrogen phosphate or a sodium salt thereof as a phosphorous source. A metal salt such as magnesium sulfate and iron sulfate may be also included. In addition, amino acids, vitamins and suitable precursors may be included.

During the culture, compounds such as ammonium hydroxide, potassium hydroxide, ammonia, phosphoric acid and sulfuric acid are expediently added to the media to control the pH value of the culture. During the culture, an antifoaming agent such as fatty acid polyglycol esters may be also used to control the development of foam.

The foreign proteins expressed in *E. coli* may exist inside the cells or may be secreted outside the cells in a variety of forms. If the foreign protein exists inside the microorganisms, a cell disruption process is performed, and then the expressed protein is bound with a primary antibody, and reacted with a fluorescent-labeled secondary antibody. The expression can be determined by color development, and protein activity or quantification can be also determined. If the expressed foreign protein is secreted outside the cells, cell pellets are separated by centrifugation, and then the results can be observed in the same manner as above.

In addition, the separation of the foreign protein from the culture may be performed by the typical method known in the art. The separation method may include centrifugation, filtration, chromatography, crystallization or the like, but is not limited thereto.

In order to facilitate the purification of the foreign protein to be recovered, the vector of the present invention may further include other sequences during construction of the vector, if necessary. The sequences further included may be tag sequences for protein purification, for example, glutathione S-transferase (Pharmacia, USA), maltose binding protein (NEB, USA), FLAG (IBI, USA), and 6×His (hexahistidine; Qiagen, USA), but the type of the sequences needed for the purification of the desired protein is not limited to these examples. The protein purification may be performed by various chromatographic methods known in the art. For example, if glutathione S-transferase is fused, its substrate glutathione may be used to perform affinity chromatography. If 6×His is used, a Ni-NTA His-bind resin column (Novagen, USA) may be used to easily recover the desired protein.

In another aspect using the vector system of the present invention, the present invention relates to a method for analyzing functions of the foreign protein, of which functions are unidentified.

In the preferred embodiment, the present invention relates to a method for analyzing functions of the foreign protein, including the steps of:

(a) culturing *E. coli* harboring the vector that sequentially includes the T7 promoter, the HA tag, and the foreign protein-encoding gene in the 5' to 3' direction; and (b) analyzing changes in characteristics and growth suppression of the *E. coli*.

In the present invention, the method for analyzing functions of the foreign protein may be used for the purpose of pre-testing the expression and function of target genes in *E. coli* before applying to mammalian cells. For example, when expression and function of the putative cell death-related genes are analyzed, or when mutant genes showing differences in the expression levels between normal and disease tissues are screened in mammals including humans by microarray, the vector system of the present invention is used to overexpress these genes in *E. coli*, and then changes in characteristics and growth suppression of the strain are examined and compared to those of normal strain, thereby rapidly pre-testing the expression and function of the genes.

Further, if the protein expressed in *E. coli* is not a human-derived protein, the method may further include a step of examining functional complementarity between the human protein and the protein expressed in *E. coli*, thereby being used for functional studies of human genes or drug screening.

In still another aspect using the vector system of the present invention, the present invention relates to a method for screening a target gene having specific functions.

In one preferred embodiment, the vector of the present invention may be applied to a screening system for selecting genes showing cytotoxicity or inducing cell death.

In the specific embodiment of the present invention, when the HtrA1 protein was expressed in *E. coli* by using the vector system of the present invention, colonies were hardly observed and cell growth suppression was observed, and the cell death was similarly induced in mammalian cells (FIGS. 3 and 4). As such, the use of the vector system of the present invention is advantageous in that cell death induction or cytotoxicity of the target gene in mammalian cells can be easily measured in *E. coli* within 10-24 hours.

Therefore, the present invention provides a composition for screening cytotoxic substances in *E. coli*, including the vector that sequentially includes the T7 promoter, the HA tag, and the gene encoding the foreign protein in the 5' to 3' direction.

Further, the present invention provides a method for screening cytotoxic substances in *E. coli* using the vector that sequentially includes the T7 promoter, the HA tag, and the gene encoding the foreign protein in the 5' to 3' direction.

In the preferred embodiment, the present invention relates to a method for screening a cytotoxic protein in *E. coli*, including the steps of:

(a) introducing *E. coli* that does not contain a T7 RNA polymerase with a vector that sequentially includes a T7 promoter, a nucleotide encoding a HA tag, and a gene encoding a foreign protein in the 5' to 3' direction;

(b) comparing growth of *E. coli* harboring the vector to that of a control strain introduced with no vector; and (c) determining the foreign protein expressed by the vector as a cytotoxic protein when the growth of *E. coli* harboring the vector is lower than that of the control strain introduced with no vector.

In the method, the control strain refers to a strain that is not harboring the vector. A wild-type strain or *E. coli* harboring an empty vector may be used.

In step (a), descriptions of the vector and *E. coli* are the same as above.

In step (b), the growth suppression of the strain may be measured by the methods known in the art. For example, the growth suppression of the strain is examined by measuring optical density using a culture broth containing the cells upon liquid culture, or by observing cell growth density with the naked eye or counting the number of colonies upon solid culture.

To compare the growth of the strain to that of the wild-type strain, for example, optical density measured upon liquid culture is analyzed by a computer program, and the effect of the drug on the control strain is determined as a reference point 0, and the growth suppression relative to the control strain is determined as a minus (−) value, thereby selecting a strain showing the value of −0.2 (20% or more) or less or a strain showing a much lower cell density than the wild-type strain upon solid culture.

This method can be used to discover proteins having cytotoxicity or promoting cell death, and the screened proteins can be used for the treatment of cell death-associated diseases, for example, a variety of cancers or infectious diseases caused by pathogenic microorganisms.

Hereinafter, the present invention will be described in detail with reference to Examples. However, these Examples are for illustrative purposes only, and the invention is not intended to be limited by the following Examples.

Example 1

Plasmid Construction

A schematic representation of various mammalian expression vectors including mature HtrA1 (M-HtrA1) gene constructed in the present invention is shown in FIG. 1a. M-HtrA1 has amino acids 150–480 of HtrA1 amino acid sequence (Genbank Accession No. NP_002766) (Kim, G. Y., et al., Biotechnol Lett, 2011. 33(7): p. 1319-26), and S328A indicates a proteolytically inactive HtrA1 generated by replacing the catalytic 328-serine residue of serine protease with alanine in M-HtrA1. pcDNA3.0 (Invitrogen (Carlsbad, Calif.)) and pCS2+(University of Michigan, Ann Arbor, Mich.) were used as a basic vector.

The plasmids used in the present invention are summarized in Table 1.

TABLE 1

| Plasmid | Basic vector[a] | Promoter | N-terminal | C-terminal | Promoter for expression in mammalian cells |
|---|---|---|---|---|---|
| pHA-M-HtrA1 | pcDNA3.0 (1) | T7 | HA | FLAG | CMV |
| pHA-M-S328A | pcDNA3.0 (1) | T7 | HA | FLAG | CMV |
| pM-HtrA1 | pcDNA3.0 (1) | T7 | — | FLAG | CMV |
| pCS-HA-M-HtrA1 | pCS2+ (2) | SP6 | HA | FLAG | sCMV |

TABLE 1-continued

| Plasmid | Basic vector[a] | Promoter | N-terminal | C-terminal | Promoter for expression in mammalian cells |
|---|---|---|---|---|---|
| pCS-M-HtrA1 | pCS2+ (2) | SP6 | — | FLAG | sCMV |
| pHA-XIAP | pcDNA3.0 (1) | T7 | HA | FLAG | CMV |
| pHA-MIF | pcDNA3.0 (1) | T7 | HA | FLAG | CMV |
| pSOD1 | pcDNA3.0 (1) | T7 | — | FLAG | CMV |
| pHA-Parkin-HA | pcDNA3.0 (1) | T7 | HA | HA | CMV |
| pMYC-Parkin-HA | pcDNA3.0 (1) | T7 | MYC | HA | CMV |

[a]the number in brackets indicates a supplier of the vector (1) Invitrogen (Carlsbad, CA); (2) Drs. David Turner and Ralph Rupp (University of Michigan, Ann Arbor, MI)

First, the HA tag base sequence (SEQ ID NO. 3) was inserted into the pcDNA3.0 vector to prepare the pcDNA3-HA plasmid (see Biochemical and Biophysical Research Communications 387 (2009) 537-542), and the pcDNA-HtrA1 plasmid provided by Dr. Alfonso Baldi (Second University of Naples, Italy) was digested with restriction enzymes pstI and XhoI, and inserted into the pBS vector to prepare the pBS-M-HtrA1 plasmid. The pcDNA3-HA and pBS-M-HtrA1 plasmids were digested with restriction enzymes EcoRI and XhoI to prepare the pHA-M-HtrA1 and pHA-M-S328A plasmids, respectively.

To prepare the pM-HtrA1 plasmid, PCR amplification was performed using pHA-M-HtrA 1 as a template (at 95° C. for 3 minutes; total 32 cycles of at 95° C. for 45 seconds, at 60° C. for 45 seconds, and at 72° C. for 1 minute, pfu DNA polymerase used; at 72° C. for 1 minute), and the following primers were used. The amplified M-HtrA1 cDNA fragment was digested with restriction enzymes EcoRI and XhoI, and then inserted into the pcDNA3.0 vector (Invitrogen, CA).

TABLE 2

| Primer | Sequence | SEQ ID NO. |
|---|---|---|
| Forward primer | AAGCTTATGCTGCAGCGCGGAGCCTGC (HindIII restriction site shown in bold, and initiation codon underlined) | 6 |
| Reverse primer | CTCGAG<u>CTA</u>*CTTGTCATCGTCGTCCTTGTA* (XhoI restriction site shown in bold, stop codon underlined, FLAG tag region in italics) | 7 |

To prepare the pCS-HA-M-HtrA1 plasmid, PCR amplification was performed using the pHA-M-HtrA1 plasmid and the following primers (at 95° C. for 3 minutes; total 32 cycles of at 95° C. for 45 seconds, at 60° C. for 45 seconds, and at 72° C. for 1 minute, pfu DNA polymerase used; at 72° C. for 1 minute). The amplified HA-M-HtrA1 cDNA fragment was digested with restriction enzymes ClaI and XhoI, and then inserted into the pCS2+ vector (Invitrogen, CA), and the product was designated as pCS-HA-M-HtrA1.

TABLE 3

| Primer | Sequence | SEQ ID NO. |
|---|---|---|
| Forward primer | ATCGATATGTACCCTTACGATGTACCG (ClaI restriction site shown in bold) | 8 |

TABLE 3-continued

| Primer | Sequence | SEQ ID NO. |
|---|---|---|
| Reverse primer | CTCGAG<u>CTA</u>*CTTGTCATCGTCGTCCTTGTA* (XhoI restriction site shown in bold, stop codon underlined, FLAG tag region in italics) | 9 |

In addition, the pHA-M-HtrA1 plasmid was digested with restriction enzymes PstI and XbaI, and the resulting fragment was inserted into pCS-M-HtrA1 GFP, and the product was designated as pCS-M-HtrA1.

To prepare the pHA-MIF plasmid, PCR was performed using a human brain cDNA library as a template and the following primers (Kim, S. S., et al., Journal of Life Science, 2005. 15(6): p. 961-7) (at 95° C. for 3 minutes; total 32 cycles of at 95° C. for 45 seconds, at 60° C. for 45 seconds, and at 72° C. for 1 minute, pfu DNA polymerase used; at 72° C. for 1 minute). The amplified MIF fragment was digested with restriction enzymes EcoR I and KpnI, and then inserted into the pcDNA-HA vector, and the product was designated as pHA-MIF.

TABLE 4

| Primer | Sequence | SEQ ID NO. |
|---|---|---|
| Forward primer | GCGCGAATTCGCCATGCCGATGTTCATCGTA (EcoRI restriction site shown in bold) | 10 |
| Reverse primer | GCGCAGATCTGGTACCGGGCGAAGGTGGAGTT (KpnI restriction site shown in bold) | 11 |

To prepare the pHA-XIAP plasmid, PCR was performed using the human brain cDNA library as a template and the following primers (at 95° C. for 3 minutes; total 32 cycles of at 95° C. for 45 seconds, at 60° C. for 45 seconds, and at 72° C. for 1 minute, pfu DNA polymerase used; at 72° C. for 1 minute). The amplified MIF fragment was digested with restriction enzymes EcoR I and KpnI, and then inserted into the pcDNA-HA vector, and the product was designated as pHA-XIAP.

TABLE 5

| Primer | Sequence | SEQ ID NO |
|---|---|---|
| Forward primer | GCGCGAATTCATGACTTTTAACAGTTTTGAA (EcoRI restriction site shown in bold) | 12 |
| Reverse primer | GCGCAGATCTGGTACCGAGACATAAAAATTTTTTGCTT (KpnI restriction site shown in bold) | 13 |

To prepare the pSOD1 plasmid, PCR was performed using the human brain cDNA library as a template and the following primers (Yoon, J. Y., et al., EMM, 2009. 41(9): p. 611-7) (at 95° C. for 3 minutes; total 32 cycles of at 95° C. for 45 seconds, at 60° C. for 45 seconds, and at 72° C. for 1 minute, pfu DNA polymerase used; at 72° C. for 1 minute). The amplified SOD1 fragment (Genbank Accession No. EF151142) was digested with restriction enzymes EcoR I and KpnI, and then inserted into the pcDNA3.0 vector, and the product was designated as pSOD1.

| Primer | Sequence | SEQ ID NO. |
|---|---|---|
| Forward primer | GCGCGAATTCATGGCGACGAAGGCCGTGTGC (EcoRI restriction site shown in bold) | 14 |
| Reverse primer | GCGCGGTACCGTTGGGCGATCCCAATTACACCA (KpnI restriction site shown in bold) | 15 |

To prepare pHA-Parkin-HA and pMYC-Parkin-HA plasmids, pMyc-Parkin-FLAG was digested with XhoI and XbaI to remove Parkin-FLAG, and the Parkin-HA fragment obtained from pBS-Parkin-HA (digested with XhoI and XbaI) was cloned into the resulting pcDNA-Myc vector. pHA-Parkin-HA was prepared by cloning the Parkin-HA fragment into the pcDNA-HA (digested with BamHI and XbaI) expression vector (Nam, M. K., et al., Journal of Life Science, 2005. 15(6): p. 916-22).

Example 2

*E. coli* Growth Analysis

The plasmid prepared in Example 1 was transformed into *E. coli* TOP10 (Invitrogen) by calcium chloride precipitation, and then *E. coli* TOP10 was seeded in LB (Luria-Bertani) broth (LB-amp broth) with ampicillin, followed by incubation at 37° C. Growth of *E. coli* was monitored by measuring optical density ($OD_{600}$) at 600 nm using a spectrophotometer (Pharmacia Biotech, UK). A growth curve graph was constructed by Sigma Plot program version 9.0. Error bars represent the standard error of the mean (SEM) of three independent experiments. Levels of statistical significance were assessed by one-way ANOVA and the Tukey post hoc comparison of means test.

DH5α and TOP10 competent cells were transformed with 1 ng of the plasmid, and cultured on LB-amp agar plates at 37° C. for 9-12 hours, respectively. The colonies were imaged using a CCD camera imaging system (Bio-Rad) and counted using Image Tool software (UTHSCSA image tool, version 2.0, ddsdx.uthscsa.edu/dig/ provided in the public domain by University of Texas Health Sciences Center, San Antonio, Tex.).

Example 3

Cell Culture and Transfection

HEK293T cells were grown in DMEM supplemented with 8.5% (v/v) heat-inactivated fetal bovine serum (Invitrogen). HEK293T cells ($2 \times 10^5$ cells/well) in 6-well plates were transfected with 1 μg of plasmid DNA (0.9 μg of target plasmid and 0.1 μg of pCS-EGFP plasmid) using 3 μl of Fugene HD (Promega) transfection reagent. At 18 hr post-transfection, the cells were stained with 4',6-diamidino-2-phenylindole (DAPI), and GFP-positive cells were analyzed for monitoring condensed or fragmented apoptotic nuclei under fluorescence microscopy (Carl Zeiss).

Example 4

Immunoblot (IB) Analysis

For immunoblot analysis of *E. coli* culture, *E. coli* culture ($OD_{600}$=0.6 or $1 \times 10^8$ cells per ml) was harvested by centrifugation at 16,100×g for 1 minute. Cells were lysed in 80 μl of 1×SDS loading buffer [58.3 mM Tris-HCl [pH 6.8], 2% SDS, 5% glycerol, 0.004% bromophenol blue, 0.05 mM EDTA, 144 mM β-mercaptoethanol] and boiled for 3 minutes.

For immunoblot analysis of HEK293T cells, transfected cells were lysed for 30 minutes on ice in a radioimmune precipitation assay buffer [20 mM Tris-HCl (pH 7.5), 150 mM NaCl, 0.1% SDS, 1% Triton X-100, 1% sodium deoxycholate] containing protease inhibitors, 10 μg/ml aprotinin, 10 μg/ml leupeptin, and 1 mM phenyl-methyl-sulfonyl fluoride. Proteins from $E.$ $coli$ ($1.8 \times 10^7$ cells, 14 μg) and HEK293T cell lysates (20 μg) were resolved by 13% SDS-PAGE and transferred to a nitrocellulose membrane. For immunoblot assays, anti-FLAG monoclonal antibody (Sigma, CA), anti-HA polyclonal antibody (Santa Cruz Biotech., CA) and anti-HtrA1 polyclonal antibody (Ab Frontier, Korea) were used. HRP (Horseradish peroxidase)-conjugated secondary anti-mouse or anti-rabbit immunoglobulin G (IgG) was purchased from Santa Cruz Biotechnology. Proteins were detected using an ECL (enhanced chemiluminescence) immunoblotting system SUPEX kit (Neuronex, Korea). The densities of target protein bands were measured by Multi Gauge V3.1 software (Fuji film).

Results

1. HtrA1 is Expressed in $E.$ $coli$ by the pHA-M-HtrA1 Mammalian Expression Vector and $E.$ $coli$ Growth is Suppressed by HtrA1 Serine Protease.

To study a human target gene in a mammalian cell system, overexpression of the target gene in mammalian cells is essential. In the present invention, human HtrA1 was selected as a target gene, and various HtrA1 constructs were prepared using pcDNA3.0 and pCS2+ vectors (FIG. 1a).

Expression of a target gene in mammalian cells is induced by the human CMV promoter (hCMV p) in the pcDNA3.0 vector, and by the simian sCMV promoter corresponding to the hCMV promoter in the pCS2+ vector. This vector contains T7 and SP6 promoters originated from bacteriophage T7 and SP6, and these promoters are oriented in opposite directions in the vector, and thus it is a multipurpose vector system used for the synthesis of sense or antisense probe through in vitro transcription. In molecular and cellular biology, target protein-specific antibodies (Ab) are essential for identification of the target protein overexpressed in mammalian cells. However, there are still limitations in the specificity of commercially available Ab or directly prepared Ab. In order to overcome the limitation, a technique of tagging a sequence encoding a short hydrophilic peptide such as HA (YPYDVPDYA, SEQ ID NO. 2), FLAG (DYKDDDDK, SEQ ID NO. 4), and MYC (EQKLISEEDL, SEQ ID NO. 5) at the N- and/or C-terminus of the target protein has been used.

In the present invention, HtrA1 was introduced in-frame with the C-terminal FLAG tag to more specifically and effectively detect expression of the mature-HtrA1 (M-HtrA1) protein. Additionally, M-HtrA1 was introduced with the N-terminal HA tag, because the mature form of HtrA1 serine protease is formed by processing, but the exact cleavage site has not yet been determined (FIG. 1a).

A large amount of plasmid DNA is needed for the transfection of mammalian cells, and thus a large amount of target plasmid DNA should be obtained through replication of the target plasmid DNA in $E.$ $coli$ system by transformation. During culture of $E.$ $coli$ harboring each plasmid for preparation of plasmid DNA, it was found that the growth of $E.$ $coli$ harboring the pHA-M-HtrA1 plasmid is largely suppressed compared with $E.$ $coli$ harboring other plasmids in LB-amp broth. For more accurate analysis, the growth of $E.$ $coli$ was compared using an agar plate and a liquid culture method.

First, 1 ng of each plasmid was transformed into $E.$ $coli$ DH5α, and then the number of colonies formed was counted to compare the growth of $E.$ $coli$. As a result, more than 100 colonies were observed in the control $E.$ $coli$ harboring pcDNA3.0, but colonies were hardly formed in $E.$ $coli$ harboring the pHA-M-HtrA1 plasmid (FIG. 1d).

Figure 1B:
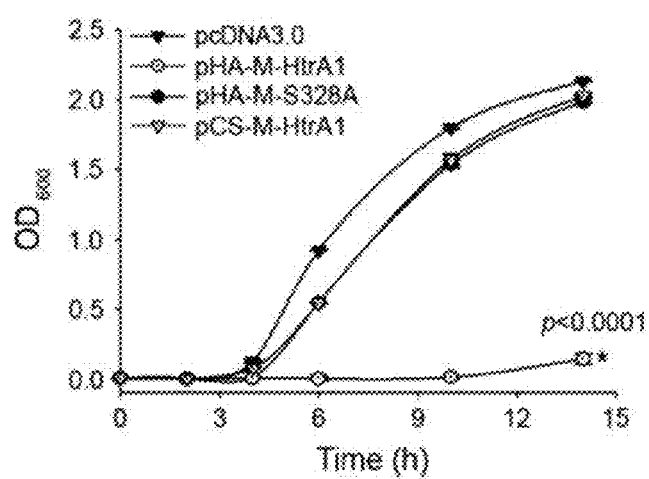
FIG. 1b is a graph showing the comparison of E. coli growth, in which optical density was measured at 600 nm after culturing E. coli introduced with a control vector (pcDNA3.0), pHA-M-HtrA1, pHA-M-S328A, and pCS-M-HtrA1.

In addition, the plasmids were transformed into another strain $E.$ $coli$ TOP10 generally used in gene cloning. To analyze time-dependent cell growth, the $E.$ $coli$ growth rate was assessed by measuring the optical density at 600 nm ($OD_{600}$) at 2 hr intervals (FIG. 1b). The number of $E.$ $coli$ cells remains relatively constant during the initial lag phase, and then $E.$ $coli$ rapidly grows to reach the exponential or log phase. In the log phase, the cell number doubles every 20-30 minutes and cell division occurs at a constant rate. In the case of the control $E.$ $coli$ harboring pcDNA3.0, $E.$ $coli$ cells were in the lag phase (prior to cell proliferation) for approximately 4 hours ($OD_{600}$=0.1), followed by exponential proliferation of the cells ($OD_{600}$=1.8 at 10 hr incubation). In contrast, the $E.$ $coli$ harboring the pHA-M-HtrA1 plasmid did not grow during 10 hr incubation and maintained the lag phase ($OD_{600}$=0.1 at 12 hr incubation), and thereafter began to grow gradually. When compared with the 6 hr cultures, the cell number of $E.$ $coli$ harboring the pHA-M-HtrA1 plasmid was approximately 0.02% of that of the control $E.$ $coli$, indicating that cell growth was suppressed by HtrA1 expression in $E.$ $coli$ harboring the pHA-M-HtrA1 plasmid.

Meanwhile, $E.$ $coli$ harboring the pHA-M-S328A plasmid that has the same pcDNA3.0 plasmid backbone as in the pHA-M-HtrA1 plasmid, but encodes a proteolytically inactive HtrA1 mutant (generated by replacing the catalytic 328-serine residue with alanine in serine protease) exhibited growth similar to the control $E.$ $coli$. Despite the presence of the wild-type HtrA1, the pCS-M-HtrA1 plasmid exhibited growth similar to the control $E.$ $coli$. These results are similar to those in $E.$ $coli$ DH5α, indicating that this phenomenon is not specific to a particular $E.$ $coli$ strain.

Figure 1C:
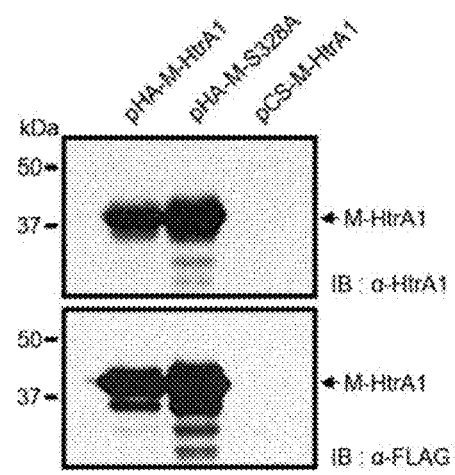
FIG. 1c is the result of immunoblot analysis of M-HtrA1 expression, when E. coli was transformed with pHA-M-HtrA1, pHA-M-S328A, pCS-M-HtrA1 and pCS-HA-M-HtrA1, respectively.
Figure 1C:
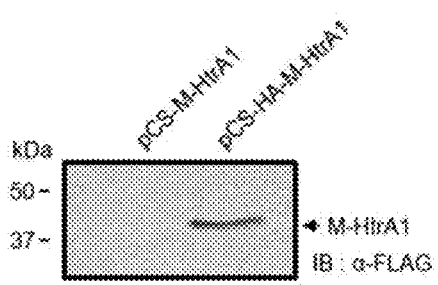
Figure 1C:
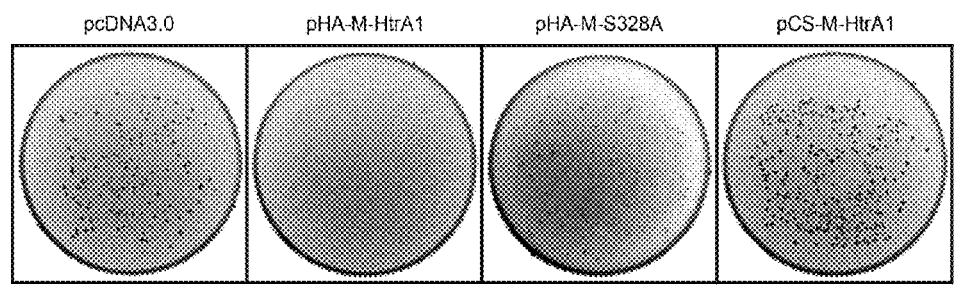

These results raise the possibility that expression of the M-HtrA1 protein may be directed from the pHA-M-HtrA1 plasmid, hence HtrA1 proteolytic activity may play a key role in the growth suppression of $E.$ $coli$. To investigate this possibility, the expression of HtrA1 was examined by immunoblot assay (FIG. 1c). When immunoblot assay was performed using FLAG antibody specific to the C-terminal FLAG tag of M-HtrA1, 39 kDa protein band was detected from $E.$ $coli$ harboring the pHA-M-HtrA1 and pHA-M-S328A plasmids, and the 39 kDa band was identified as M-HtrA1 by using HtrA1-specific anti-HtrA1 antibody. However, it was found that M-HtrA1 was not expressed from the pCS-M-HtrA1 plasmid.

These results demonstrate that expression of the M-HtrA1 protein in $E.$ $coli$ is driven by the pHA-M-HtrA1 plasmid mammalian expression vector that could not be used to direct expression of the target protein in $E.$ $coli$, and induces the growth suppression of $E.$ $coli$ in an HtrA1 serine protease-dependent manner.

2. T7 Promoter and Nucleotide Sequences Encoding a 5'-Adjacent HA Tag in the Expression Vector are Required for the Target Gene Expression in $E.$ $coli$ The expression vectors used in a mammalian model system contain CMV promoter or sCMV promoter, and bacteriophage T7, SP6 promoters to drive in vitro transcription. Because endogenous $E.$ $coli$ RNA polymerase has little specificity on T7/SP6 promoters, T7/SP6 promoter-driven gene transcription is known to rarely occur in $E.$ $coli$ TOP10 and $E.$ $coli$ DH5α lacking T7/SP6 RNA polymerase. Unexpectedly, it was found that the pHA-M-HtrA1 mammalian expression vector system can be used to direct expression of HtrA1 in *E. coli*, which raises the possibility that certain elements responsible for the human target gene expression exist within the pHA-M-HtrA1 mammalian expression vector.

Figure 2A:
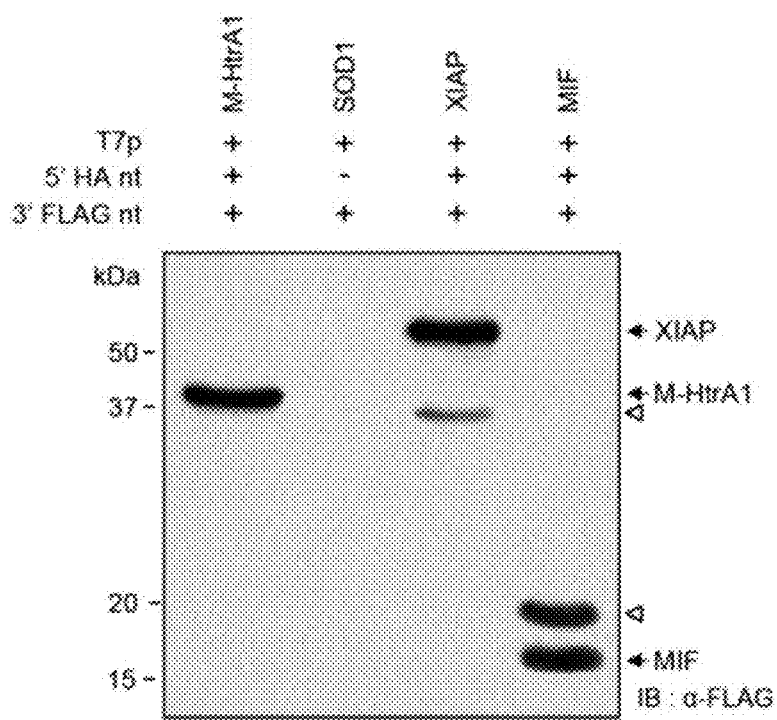
FIG. 2a is the result of immunoblot analysis of protein expression in E. coli, in which the target gene was replaced with XIAP and MIF (pHA-XIAP and pHA-MIF), and replaced with SOD1 and HA tag was removed (pM-SOD1) in the pHA-M-HtrA1 plasmid, and open arrowheads indicate non-specific bands, and + and − indicate presence and absence of tag or T7 promoter.

In order to investigate whether this phenomenon is specific to HtrA1, different target genes were replaced with HtrA1 in the pHA-M-HtrA1 plasmid and the expression of target genes in *E. coli* was determined by immunoblot assay (FIG. 2a). Like the HtrA1 results, XIAP (X-linked inhibitor of apoptosis protein) and MIF (macrophage migration inhibitory factor) with HA tag were expressed in *E. coli*, whereas SOD1 (superoxide dismutase 1) without HA tag was not expressed despite the existence of the T7 promoter. Although M-HtrA1 expression was not observed from the pCS-M-HtrA1 plasmid, which contains the 5' terminal SP6 promoter, lower levels of the M-HtrA1 expression could be detected from the pCS-HA-M-HtrA1 containing the N-terminal HA tag, exhibiting approximately 20 times lower than expression levels driven by the pHA-M-HtrA1 plasmid (FIG. 1c).

Figure 2B:
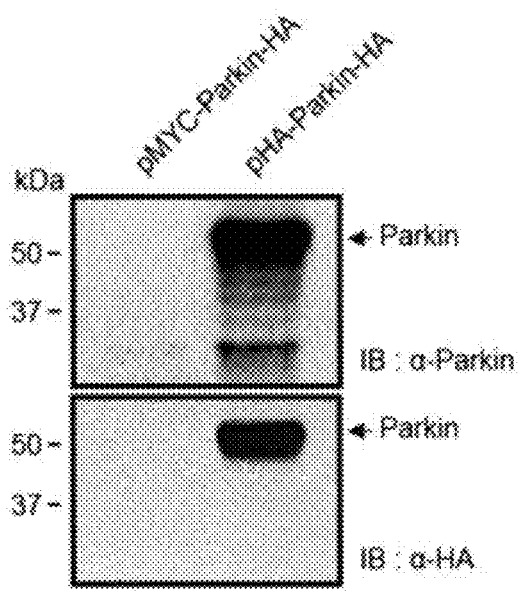
FIG. 2b is the result of immunoblot analysis of protein expression in E. coli, in which Parkin expression vectors including N-terminal HA tag (pHA-Parkin-HA) and N-terminal MYC tag (pMYC-Parkin-HA) in pcDNA3.0 backbone were used.

Subsequently, to investigate whether the target gene expression is specific to the nucleotide sequence encoding HA tag, expression of Parkin with N-terminal HA and MYC tags, which is driven by the same pcDNA3.0 vector backbone, was assessed by immunoblot assay (FIG. 2b). The expression of Parkin was observed in the HA-tagged vector, but not in the MYC-tagged vector.

These results indicate that the T7 promoter used for in vitro transcription in the mammalian expression vector system and the nucleotide sequences encoding the HA tag used for the detection of protein expression are essential cis-acting elements that can direct the expression of target genes in *E. coli*, and also indicate that this phenomenon is not specific to HtrA1, but generally occurs in different target genes.

Although the exact action mechanism of this phenomenon has not yet been elucidated, it is suggested that the HA-encoding nucleotide sequence located downstream of T7 promoter functions to strengthen the ability of *E. coli* RNAP to recognize T7 promoter or to increase processivity, leading to an increase in target gene expression.

3. The pHA-M-HtrA1 Mammalian Expression Vector is a Valuable System for Evaluating the Expression and Functions of a Human Target Gene in *E. coli*

Generally, it takes at least 1 week to investigate expression and function of the target genes in mammalian cells after cloning of the target genes into mammalian expression vectors. In addition, when transfection is performed in mammalian cells after cloning of the target genes into the expression vector system, expression of the target proteins could not be detected in some cases. Therefore, there is a need to develop a system for minimizing the experiment time and more efficiently evaluating the expression of cloned vector.

The results of the present invention suggest the possibility that the pHA-M-HtrA1 mammalian expression vector will be applied as a pre-test system for expression and function (e.g., cytotoxicity) of target genes in *E. coli* before applying it to mammalian cells, as well as its use in mammalian cells.

Figure 3A:
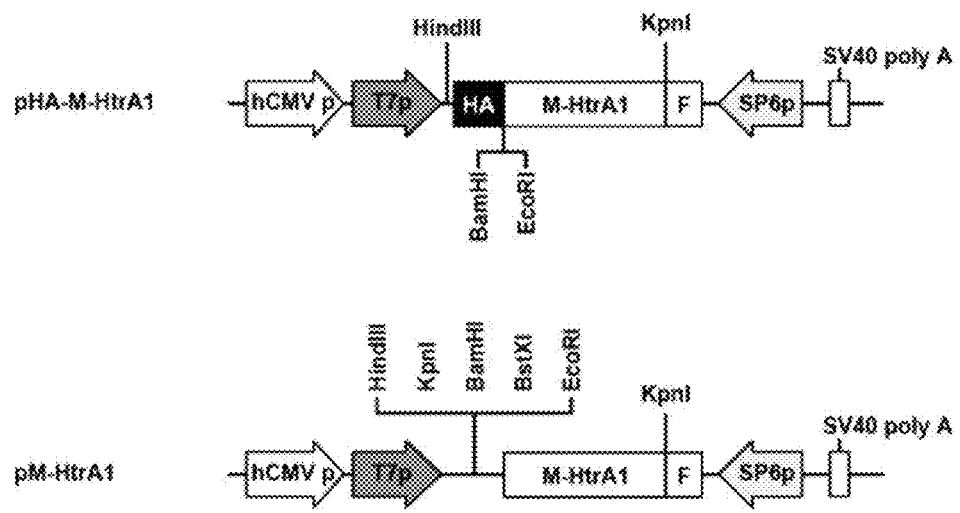
FIG. 3a is a schematic representation of pHA-M-HtrA1 and pM-HtrA1 plasmids.
Figure 3B:
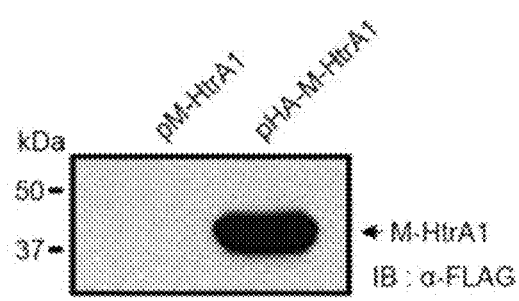
FIG. 3b is the result of immunoblot analysis of M-HtrA1 expression, when E. coli was transformed with pHA-M-HtrA1 and pM-HtrA1, respectively.
Figure 3C:
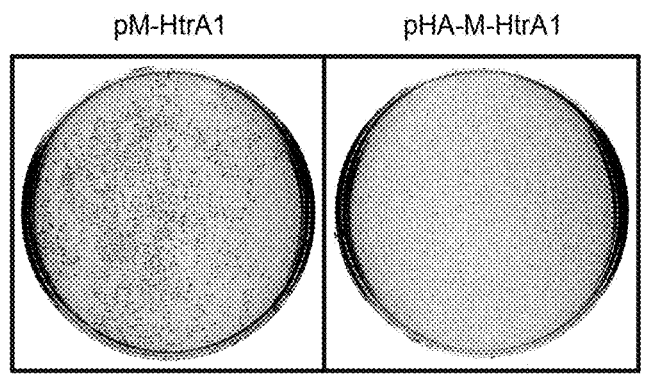
FIG. 3c is the result showing the comparison of E. coli growth, in which pHA-M-HtrA1 and pM-HtrA1 were transformed into E. coli, respectively and then the number of colonies formed was counted.
Figure 4A:
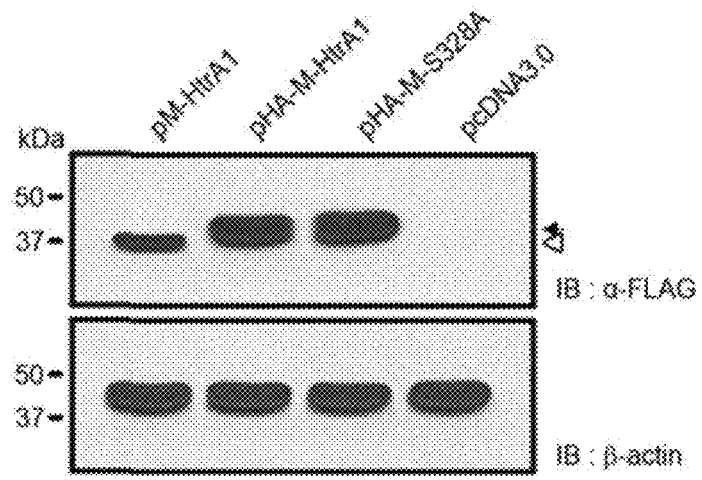
FIG. 4a is the result of immunoblot analysis of M-HtrA1 expression, when HEK293T was transfected with the control vector (pcDNA3.0), pHA-M-HtrA1, pM-HtrA1 and pCS-M-HtrA1, respectively.

To test this possibility, the present inventors comparatively analyzed the expression and cytotoxicity of HtrA1 in both *E. coli* (FIG. 3) and mammalian cells (FIG. 4). First, to further confirm whether the presence of the T7 promoter and the N-terminal HA tag in the pcDNA3.0 plasmid affects the expression of HtrA1 in *E. coli* and the growth of *E. coli*, the pM-HtrA1 plasmid was constructed by removing the HA tag-encoding nucleotide sequence from the pHA-M-HtrA1 plasmid (FIG. 3a). Unlike the pHA-M-HtrA1 plasmid, expression of HtrA1 from the pM-HtrA1 plasmid was not observed in *E. coli* (FIG. 3b). Furthermore, the number of colonies formed was found to be similar to that in *E. coli* harboring the control vector due to no effect of HtrA1 on the *E. coli* growth (FIG. 3c).

Figure 4B:
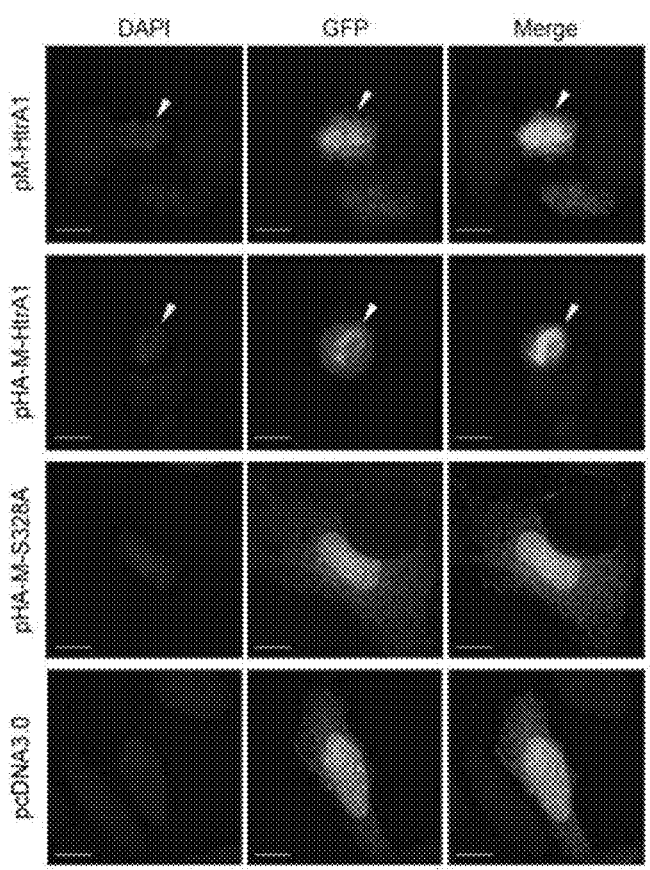
FIG. 4b is the result of DAPI staining showing whether cell death occurs when HEK293T was transfected with the control vector (pcDNA3.0), pHA-M-HtrA1, pM-HtrA1 and pCS-M-HtrA1, respectively, in which scale bar=10 μm and white arrowhead indicates dead cells induced by HtrA1

In order to examine whether the pHA-M-HtrA1 and pM-HtrA1 plasmids operate in mammalian cells, the plasmids were transfected into HEK293T cells to evaluate the expression and cytotoxicity of HtrA1 by DAPI staining. As a result, the expression of 37-kDa M-HtrA1 from both plasmids was detected in HEK293T (FIG. 4a), and cell death was similarly included (FIG. 4b).

In conclusion, our data demonstrate for the first time that expression of the human target genes in *E. coli* is directed by the combination of both the T7 promoter and nucleotide sequences encoding the N-terminal HA tag. On the basis of this result, the pHA-M-HtrA1 mammalian expression vector system can be applied as a vector system to pre-test the expression of the target gene in mammalian cells, because the expression of the target protein in *E. coli* can be easily measured within 24 hours. Further, the pHA-M-HtrA1 mammalian expression vector system can be applied as a pre-test system, because cell death induction or cytotoxicity of the target gene in mammalian cells can be rapidly diagnosed in *E. coli* within 10~24 hours. Furthermore, the present invention may provide new insight into the problem of growth suppression of *E. coli* that can occur in molecular biology research, such as molecular cloning of the mammalian expression vector system.

EFFECT OF THE INVENTION

The use of the vector system of the present invention allows T7 promoter-driven expression of foreign protein in *E. coli* using its endogenous gene expression system in the absence of T7 RNAP, and thus the vector is useful for functional studies of proteins or for mass-production of useful proteins, and furthermore useful for screening target functional genes.

What is claimed is:

1. A method for producing a foreign protein, comprising the step of culturing *E. coli* (*Escherichia coli*) that contains a vector sequentially including a T7 promoter, a nucleotide encoding an HA tag and a gene encoding a foreign protein in the 5' to 3' direction, and does not contain a T7 RNA polymerase.

2. The method according to claim 1, wherein the *E. coli* is DH5α strain or TOP10 strain.

3. The method according to claim 1, wherein the T7 promoter has a nucleotide sequence of SEQ ID NO. 1.

4. The method according to claim 1, wherein the HA tag has an amino acid sequence of SEQ ID NO. 3.

5. The method according to claim 1, wherein the foreign protein is a human-derived protein.

6. The method according to claim 5, wherein the human-derived protein is selected from the group consisting of peptides, polypeptides, binding proteins, binding domains, adhesion proteins, structural proteins, regulatory proteins, toxin proteins, enzymes, enzyme inhibitors, hormone, hormone analogues, antibodies, signal transduction proteins, single chain antibodies, antigens, cytokines, regulators, and parts thereof.

7. The method according to claim 6, wherein the human-derived protein is HtrA1 (high temperature requirement protein A1), XIAP (X-linked inhibitor of apoptosis protein), MIF (macrophage migration inhibitory factor) or Parkin protein.

* * * * *

SEQUENCE LISTING

<160> NUMBER OF SEQ ID NOS: 15

<210> SEQ ID NO 1
<211> LENGTH: 20
<212> TYPE: DNA
<213> ORGANISM: Bacteriophage T7
<220> FEATURE:
<221> NAME/KEY: promoter
<222> LOCATION: (1)..(20)
<223> OTHER INFORMATION: T7 promoter

```
<400> SEQUENCE: 1
taatacgact cactataggg                                                   20

<210> SEQ ID NO 2
<211> LENGTH: 9
<212> TYPE: PRT
<213> ORGANISM: Artificial Sequence
<220> FEATURE:
<223> OTHER INFORMATION: Amino acid sequence of HA tag

<400> SEQUENCE: 2

Tyr Pro Tyr Asp Val Pro Asp Tyr Ala
 1               5

<210> SEQ ID NO 3
<211> LENGTH: 27
<212> TYPE: DNA
<213> ORGANISM: Artificial Sequence
<220> FEATURE:
<223> OTHER INFORMATION: Nucleic acid sequence of HA tag

<400> SEQUENCE: 3
tacccttacg atgtaccgga ttacgca                                           27

<210> SEQ ID NO 4
<211> LENGTH: 8
<212> TYPE: PRT
<213> ORGANISM: Artificial Sequence
<220> FEATURE:
<223> OTHER INFORMATION: FLAG tag

<400> SEQUENCE: 4

Asp Tyr Lys Asp Asp Asp Asp Lys
 1               5

<210> SEQ ID NO 5
<211> LENGTH: 10
<212> TYPE: PRT
<213> ORGANISM: Artificial Sequence
<220> FEATURE:
<223> OTHER INFORMATION: MYC tag

<400> SEQUENCE: 5

Glu Gln Lys Leu Ile Ser Glu Glu Asp Leu
 1               5                  10

<210> SEQ ID NO 6
<211> LENGTH: 27
<212> TYPE: DNA
<213> ORGANISM: Artificial Sequence
<220> FEATURE:
<223> OTHER INFORMATION: forward primer

<400> SEQUENCE: 6
aagcttatgc tgcagcgcgg agcctgc                                           27

<210> SEQ ID NO 7
<211> LENGTH: 30
<212> TYPE: DNA
<213> ORGANISM: Artificial Sequence
<220> FEATURE:
<223> OTHER INFORMATION: reverse primer

<400> SEQUENCE: 7
ctcgagctac ttgtcatcgt cgtccttgta                                        30
```

<210> SEQ ID NO 8
<211> LENGTH: 27
<212> TYPE: DNA
<213> ORGANISM: Artificial Sequence
<220> FEATURE:
<223> OTHER INFORMATION: forward primer

<400> SEQUENCE: 8
atcgatatgt acccttacga tgtaccg                                27

<210> SEQ ID NO 9
<211> LENGTH: 30
<212> TYPE: DNA
<213> ORGANISM: Artificial Sequence
<220> FEATURE:
<223> OTHER INFORMATION: reverse primer

<400> SEQUENCE: 9
ctcgagctac ttgtcatcgt cgtccttgta                             30

<210> SEQ ID NO 10
<211> LENGTH: 31
<212> TYPE: DNA
<213> ORGANISM: Artificial Sequence
<220> FEATURE:
<223> OTHER INFORMATION: forward primer

<400> SEQUENCE: 10
gcgcgaattc gccatgccga tgttcatcgt a                           31

<210> SEQ ID NO 11
<211> LENGTH: 32
<212> TYPE: DNA
<213> ORGANISM: Artificial Sequence
<220> FEATURE:
<223> OTHER INFORMATION: reverse primer

<400> SEQUENCE: 11
gcgcagatct ggtaccgggc gaaggtggag tt                          32

<210> SEQ ID NO 12
<211> LENGTH: 31
<212> TYPE: DNA
<213> ORGANISM: Artificial Sequence
<220> FEATURE:
<223> OTHER INFORMATION: forward primer

<400> SEQUENCE: 12
gcgcgaattc atgactttta acagttttga a                           31

<210> SEQ ID NO 13
<211> LENGTH: 38
<212> TYPE: DNA
<213> ORGANISM: Artificial Sequence
<220> FEATURE:
<223> OTHER INFORMATION: reverse primer

<400> SEQUENCE: 13
gcgcagatct ggtaccgaga cataaaaatt ttttgctt                    38

<210> SEQ ID NO 14
<211> LENGTH: 31
<212> TYPE: DNA
<213> ORGANISM: Artificial Sequence
<220> FEATURE:
<223> OTHER INFORMATION: forward primer

```
<400> SEQUENCE: 14
gcgcgaattc atggcgacga aggccgtgtg c                              31

<210> SEQ ID NO 15
<211> LENGTH: 33
<212> TYPE: DNA
<213> ORGANISM: Artificial Sequence
<220> FEATURE:
<223> OTHER INFORMATION: reverse primer

<400> SEQUENCE: 15
gcgcggtacc gttgggcgat cccaattaca cca                            33
```